United States Patent [19]

Joyce

[11] 4,074,687
[45] Feb. 21, 1978

[54] METHOD OF AND APPARATUS FOR USE IN GENERATING LIQUID CONCENTRATION GRADIENTS HYDROSTATICALLY

[76] Inventor: John E. Joyce, 22 Nelson Road, South Weymouth, Mass. 02190

[21] Appl. No.: 701,173

[22] Filed: June 30, 1976

[51] Int. Cl.² .............................................. G05D 11/03
[52] U.S. Cl. ........................................ 137/266; 137/1; 137/604
[58] Field of Search ............................ 137/1, 266, 604

[56] References Cited

U.S. PATENT DOCUMENTS

| | | | |
|---|---|---|---|
| 1,335,093 | 3/1920 | Copetta | 137/266 |
| 3,344,801 | 10/1967 | Bessman | 137/266 X |
| 3,840,040 | 10/1974 | Joyce | 137/266 X |

Primary Examiner—Robert G. Nilson

[57] ABSTRACT

A hydrostatic gradient generator has a first liquid chamber and a second liquid chamber detachably attached to a base provided with a pressure regulator. The regulator has inlets, one for each chamber and in communication with the lower end thereof with the two inlets opening into the regulator close to its upper end and at the same level to provide a pressure reference plane inclusive of the bottom of the gradient producing portion of the liquid in the second chamber. The portions of the chambers for the gradient forming volumes are of the same volumetric capacity with their cross sectional areas constantly increasing from a minimum at one end to a maximum at the other end, the minimum at the lower end of the first chamber and the maximum at the lower end of the second chamber. Means are provided to enable the first chamber to be offset vertically relative to the second chamber. As the pressure at a given depth in a liquid body is equal to the density of the liquid times the distance to that depth from a free surface, an appropriate lesser volume of liquid in the second chamber will result in initial flow from the first chamber. With equal volumes of gradient forming liquids the first chamber is raised until the product of the height and density of the liquid therein is at least equal to the product of the height and density of the liquid in the second chamber. The flow, however, may initiate from the first chamber or the second chamber or it may flow simultaneously from both depending on the height and density relationship of the two liquids relative to the common pressure reference plane.

15 Claims, 10 Drawing Figures

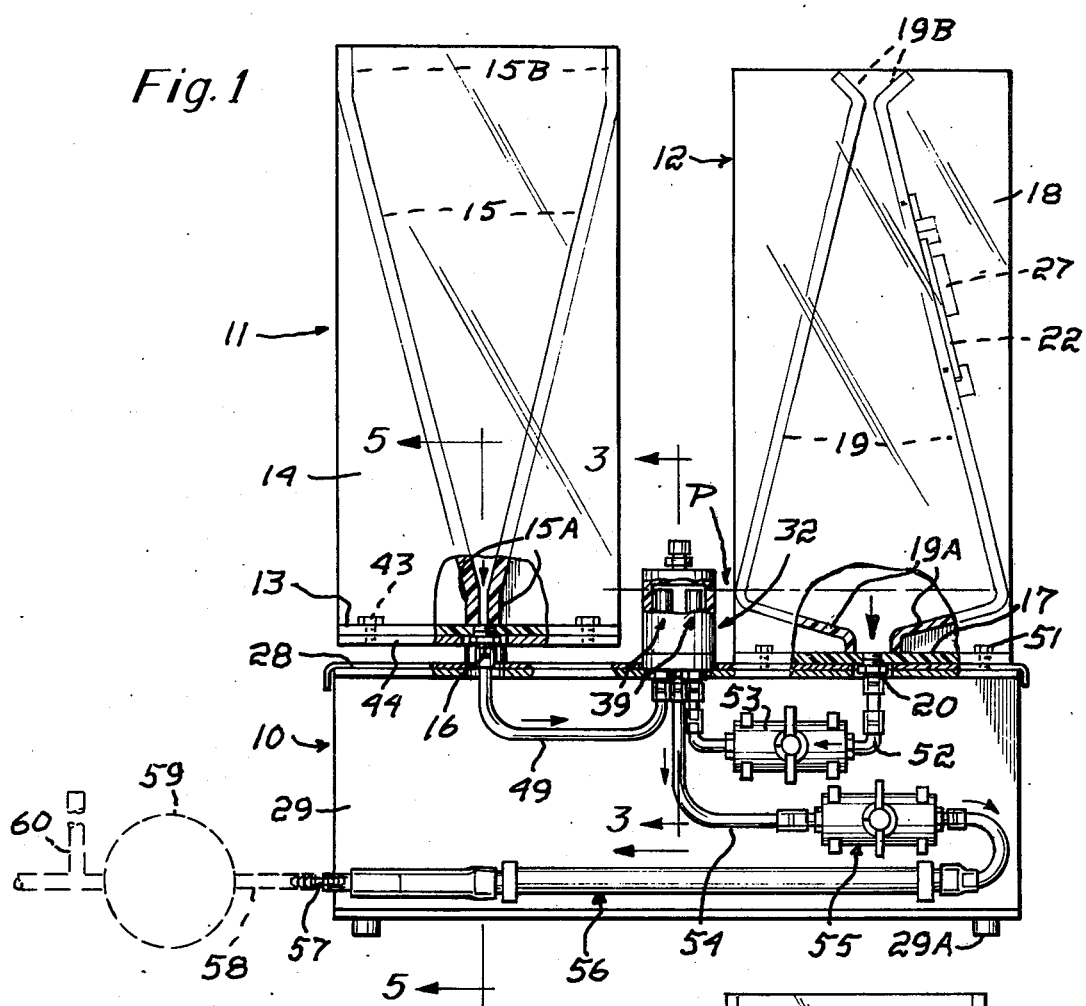
Fig.1
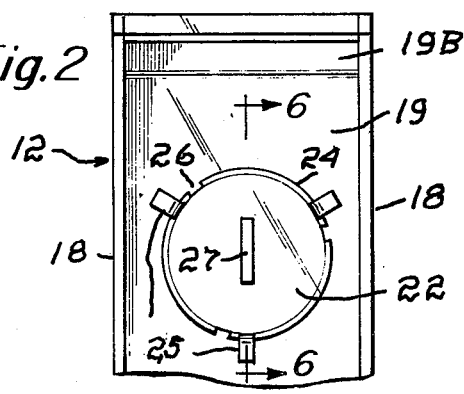
Fig.2
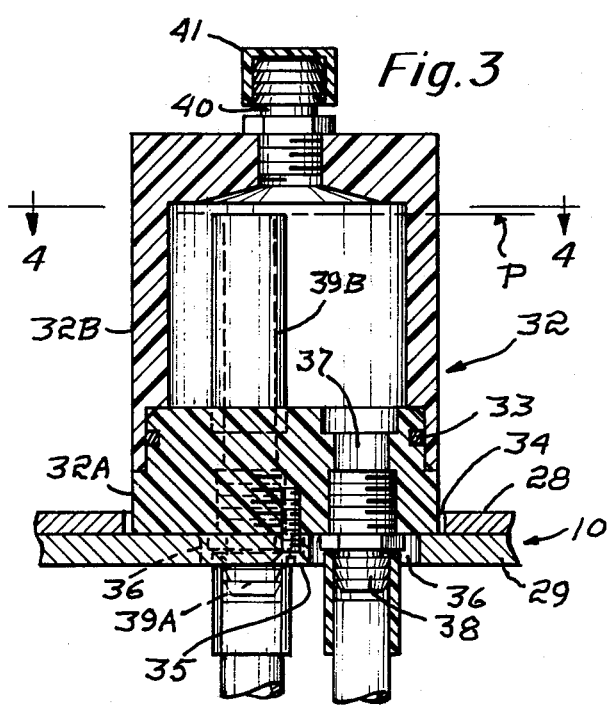
Fig.3
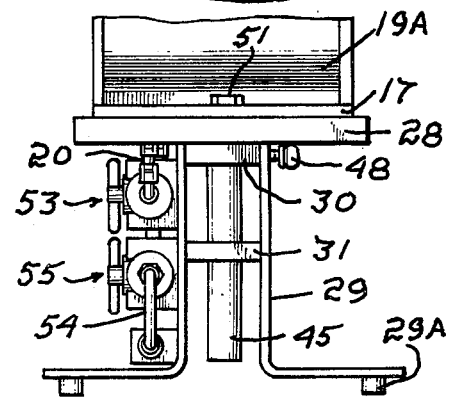

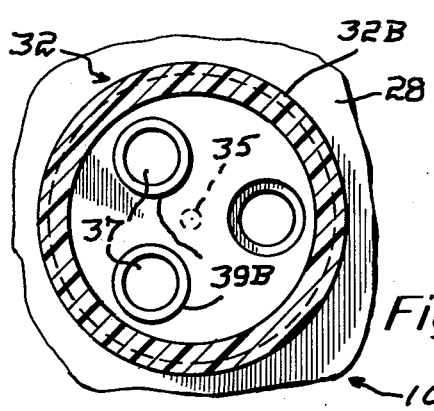
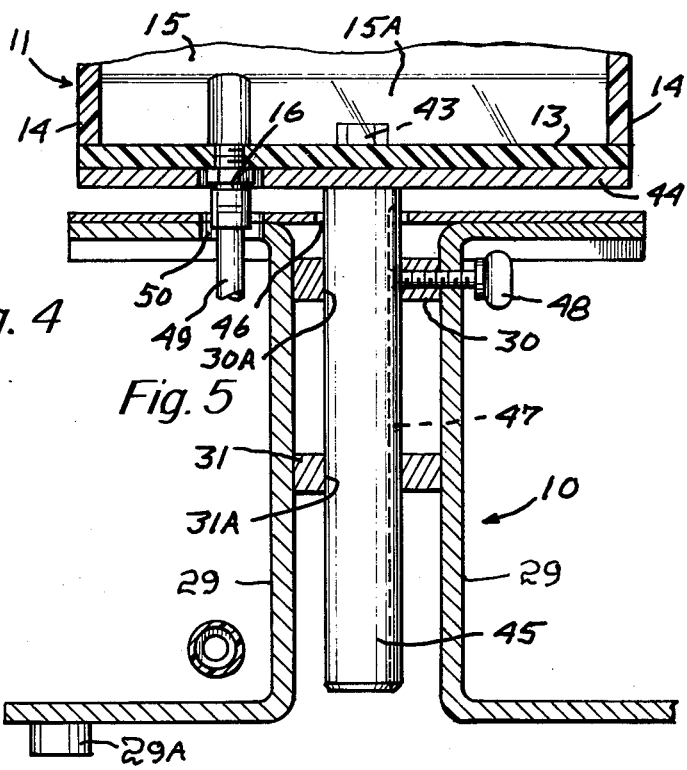
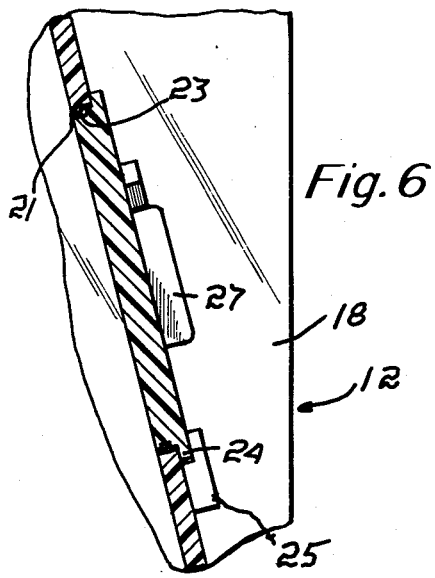
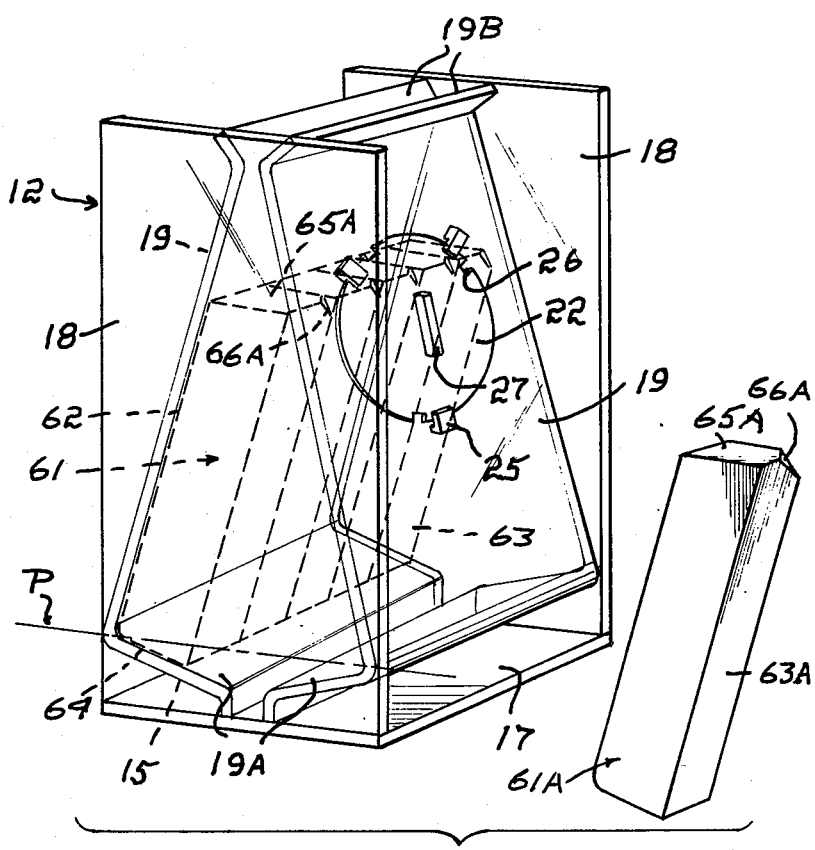

NORMALIZED GRADIENT CURVES FOR HYDROSTATIC GRADIENT GENERATORS

RELATIONSHIP OF DRAINING CHAMBERS

METHOD OF AND APPARATUS FOR USE IN GENERATING LIQUID CONCENTRATION GRADIENTS HYDROSTATICALLY

BACKGROUND REFERENCE

U.S. Pat. No. 3,840,040

BACKGROUND OF THE INVENTION

The generation of a concentration gradient of two liquids is effected, as is well known, by continuously mixing two liquids of different densities with the resulting flow comprising a continuously increasing volume of one liquid and a corresponding continuously decreasing volume of the other liquid. Gradients may be of other shapes than linear and their slopes are determined by the shape of the gradient producing portion of the chambers in which the required volumes of the two liquids are contained. For many purposes, gradient generators prior to the present invention meet requirements.

In the case of fractionators in accordance with U.S. Pat. No. 3,862,029, by way of example, relatively large volumes of a gradient are used, twelve liters each time. In addition, such a gradient must be capable of being accurately and consistently reproduced with the further requirement that such a volume of a gradient be generated in a convenient time frame, approximately 25 minutes, for one example.

Existing gradient generators are inadequate in terms of one or more of the following requirements: volume, time required for the generation of that volume, and ability consistently and accurately to reproduce a particular gradient. In addition, a gradient generator of an existing type that may not be inadequate for any one of the foregoing considerations, would be too expensive to permit wide acceptance in any field where the other conditions were also important.

THE PRESENT INVENTION

The general objective of the present invention is to provide a method of and a generator for use in forming liquid concentration gradients hydrostatically, an objective attained, in terms of apparatus, with a generator having a first chamber for one liquid and a second chamber for a different liquid and providing for the adjustment of one liquid relative to the other such that the liquid levels may result in an appropriate hydrostatic relationship with regard to the differences in the densities of the two liquids.

The portions of the chambers that are to hold the gradient-forming volumes are of the same capacity and of cross sectional shapes that decrease in area in the prescribed manner with a maximum at one end to a minimum at the other. The chambers are disposed vertically with the small end of that portion of the first chamber and the large end of that portion of the second chamber at the bottoms thereof.

The generator includes a pressure regulator having inlets, one for each chamber and in communication with the bottom thereof, and a bottom outlet, the outlet connected to a valve controlled, gradient delivery conduit. The pressure regulator is a small, sealed chamber and the two inlets have vertical portions opening therein close to the upper end thereof and in the same horizontal plane that is a pressure reference plane inclusive of the bottom of that portion of the second chamber that contains the gradient forming volume of the second liquid.

Another important objective of the invention is to provide such a generator with means enabling the first liquid chamber to be so positioned vertically relative to the pressure reference plane as to provide control of flow into the pressure regulator in the desired gradient forming manner in spite of different densities of the two liquids.

In terms of method, these general objectives of the invention are attained by confining gradient forming volumes of the first and second liquids in the chambers of the same size and shape such that the cross sectional area of each volume increases in a vertical direction from a maximum to a minimum in the same manner, the minimum cross sectional area of the first liquid volume at the bottom thereof and the maximum cross sectional area of the second liquid volume at the bottom thereof, providing a drainage path from the bottom of each contained volume with the outlet ends of each path opening in the same plane close to the upper end of a small sealed chamber and inclusive of the maximum cross sectional area of the second liquid volume, providing a drainage path from the bottom of the small chamber, and establishing a liquid level relationship between the two volumes that provides the appropriate hydrostatic relationship, if the densities of the two liquids differ, that results in a desired, gradient-forming flow into and through the small chamber. In the usual case, the liquid levels of the two volumes is such that the product of the height of the first liquid body relative to said plane and its density is at least equal to the product of the height of the liquid body drom said plane times its density, and then draining the two chambers via the sealed chamber until at least the first liquid volume is spent.

Another important objective of the invention, in terms of method, is to provide the additional step of positioning the first chamber volume relative to the pressure reference plane to control the effect of the different densities of the two liquids to provide a wanted flow.

Since the pressure at a given depth in a liquid is equal to the density of the liquid times the distance to that depth from a free surface, the height of the liquid in either chamber is equal to the pressure in the pressure regulator divided by the density of the liquid in that chamber. By adjustments of the first chamber vertically relative to the second chamber in proportion to the ratio between their densities and with the level of the liquids in both inlets of the regulator the same, the liquids in both chambers are subject to the same pressure by the pressure regulator so long the ratio of the height of the liquids in the chambers is inverse to the ratio of the respective densities of the two liquids. Since the volume, per unit height of either chamber, is a function of its cross sectional area at any given height, the volumetric output of each chamber required to maintain the hydrostatic relationship varies with the cross sectional area as the level of that liquid drops, that of the first chamber decreasing and that of the second chamber increasing. As each chamber drains, the ratio of the volumes combining in the pressure regulator changes continuously in accordance with the height relationship providing a concentration gradient that is a density gradient if the densities of the two liquids differs.

An important objective of the invention in terms of both apparatus and method is that of ensuring that one liquid cannot flow into the chamber from the other liquid, an objective attained, once the pressure reference plane is established with its outlet closed since the liquid level in the pressure regulator is then maintained by the pressure in the pressure regulator when both chambers are draining.

While an important objective of the invention is to provide for the generation of gradients that are linear, another objective of the invention is to provide for the generation of gradients of other shapes, an objective attained by providing the generator with a base to which the first and second liquid chambers are detachably attached. The pressure regulator is mounted on the base with its inlets detachably connected to the chambers and the outlet, delivery conduit, valves and, desirably a mixer, all attached to the base so that chambers of shapes and volumetric capacities required for the production of gradients of other shapes and volumes can be attached to the base and utilize the components of the invention connected thereto in generating such other gradients.

Another objective of the invention is concerned with the means to raise and lower the first chamber relative to the second chamber, an objective attained by providing the base with a mount to which the first chamber is detachably attached and which includes a member supported by the base for movement vertically relative thereto and with the base also having means by which the member may be locked in any selected vertical position of the mount.

Another objective of the invention is concerned with the provision of a pressure regulator that will make easy the correct operation of the generator, an objective attained with a pressure chamber having its outlet in its bottom and the two inlets extending upwardly therethrough and opening into the pressure chamber relatively near its closed upper end, the upper end desirably having a normally closed port.

Yet another objective of the invention is to provide an arrangement of inlet and outlet conduits that will enable the operation of the generator to be easily monitored, an objective attained by providing that the outlet and the inlets and the delivery conduit are transparent, flexible tubing positioned, together with the valves, on the front of the base so that liquid levels and the flow of the liquids can be observed and easily controlled.

Yet another objective of the invention is to provide chambers adapted to meet various requirements of production and use, an objective attained with chambers including bottom walls and vertical end walls and side walls, the side walls in that portion of both chambers that is to contain the gradient forming volume inclined in the same manner so that their cross sectional areas constantly increase from a minimum at one end to a maximum at the other. In the case of the first liquid chamber, the minimum cross sectional area of that portion is at the bottom thereof and in the case of the second liquid chamber, the maximum cross sectional area of that portion is at the bottom thereof.

The upper end of the side walls of the first chamber include short vertical portions while the lower ends of the second chamber side walls slant slightly downward and inward. The corresponding side walls of the first chamber at their lower ends are brought nearly together providing a neck while the upper ends of the side walls of the first chamber include short, oppositely inclined portions providing a mouth or funnel to facilitate the pouring of liquid into it.

Another objective of the invention is to enable gradients of a smaller volume to be generated without replacing chambers for use in producing a larger volume of a gradient of the same shape, an objective attained by providing a second liquid chamber with a removable part enabling an insert to be placed therein that will reduce the portion for the gradient forming volume to a desired extent without changing its shape. The insert fits between the end walls of the second chamber and has parallel side walls of which one side is seated against a chamber side wall, a lower end seated against the proximate lower end of that side wall, and an upper end in contact with the other side wall of the chamber at a predetermined height above a horizontal plane inclusive of the junctions of the chamber side walls with their lower ends.

Another objective of the invention is to provide easily operated sealed means for permitting manual access to the interior of the second chamber, an objective attained with one side wall thereof having a porthole normally closed by a sealed plug and a specific objective is to provide an insert for a chamber having that feature, the insert consisting of a series of identical sections, each dimensioned to be placed manually in position within the chamber through the porthole.

BRIEF DESCRIPTION OF THE DRAWINGS

A preferred embodiment of a hydrostatic gradient generator is illustrated by the accompanying drawings and FIG. 1 is a partly sectioned front view of a generator in accordance with the invention;

FIG. 2 is a view of the generator as seen from the second liquid chamber end thereof;

FIG. 3 is a section on an increase in scale taken approximately along the indicated line 3—3 of FIG. 1;

FIG. 4 is a section taken approximately along the indicated lines 4—4 of FIG. 3;

FIG. 5 is a fragmentary section, on an increase in scale, taken approximately along the lines 5—5 of FIG. 1;

FIG. 6 is a section, on an increase in scale, taken approximately along the lines 6—6 of FIG. 2;

FIG. 7 is a fragmentary view showing the connection of a syringe to the port in the upper end of the pressure regulator;

FIG. 8 is a perspective view of the second chamber with an insert therein by which the volume of its portion that is to contain the gradient forming portion of a second liquid is reduced without changing the shape thereof;

THE PREFERRED EMBODIMENT OF THE INVENTION

Figure 9:
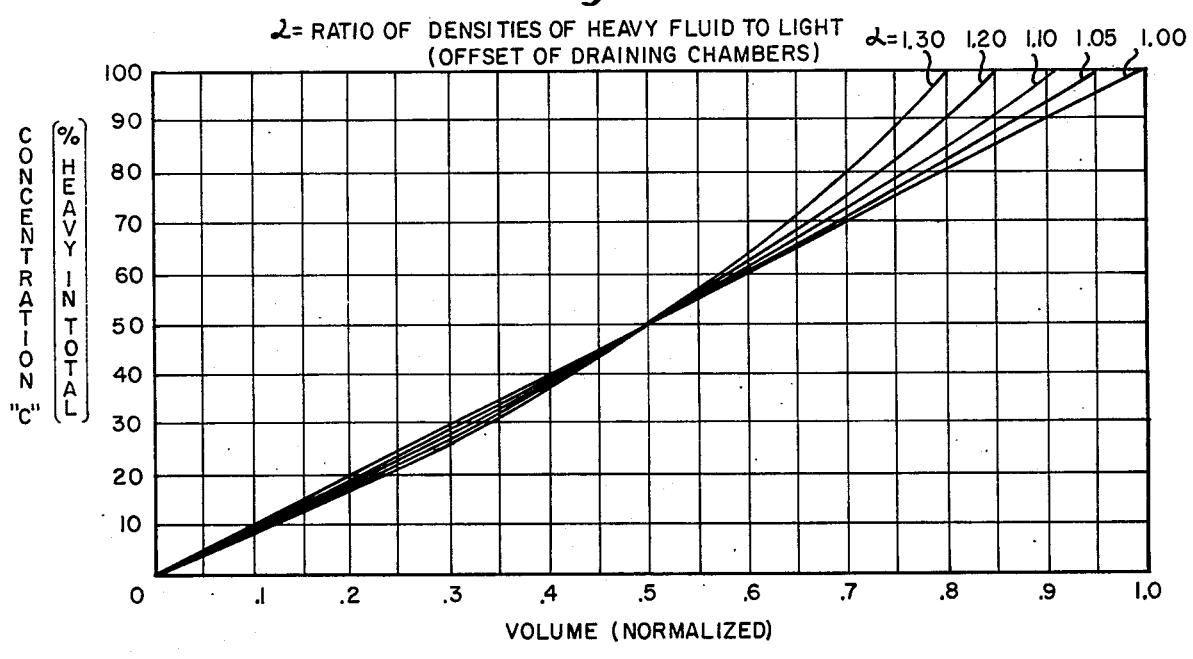
FIG. 9 is a graph showing typical gradient curves.

The hydrostatic generator illustrated by the drawings has a base, generally indicated at 10, and first and second chambers, generally indicated at 11 and 12, respectively, the first chamber 11 to accommodate a predetermined volume of a first liquid and the second chamber 12 for the same volume of a second liquid. The invention is herein discussed with the generation of liquid concentration gradients hydrostatically where the first liquid is light and the second liquid heavier.

The chambers 11 and 12 are shown for use when the generator is to produce a linear gradient and are sufficiently dissimilar to warrant their being separately described. It should be noted however that they are desirably formed of clear stock and are adapted to be easily attached to and removed from the base 10, then to be replaced by other first and second generally similar chambers but of approximately different shape-volume characteristics required to generate gradient shapes other than linear and/or of different volumes.

The chamber 11 has a base or bottom 13, vertical front and rear end walls 14, shown as rectangular, and side wall 15. The side walls 15 are upwardly and outwardly inclined so that the cross sectional area of the chamber 11 continually increases from its lower end where vertical portions 15A define a narrow outlet to a maximum at its upper end at their junction with vertical upper end portions 15B. That part of the chamber 11 below a plane inclusive of the junction of the walls 15 with the end portions 15B is for the volume of light liquid to be used in forming the gradient. The chamber bottom 13 has a depending outlet 16 opening into the outlet 15A and located relatively near the front wall 14.

The chamber 12 has a base or bottom 17, front and rear end walls 18, shown as rectangular, and side walls 19. The side walls 19 are inclined upwardly and inwardly so that their cross sectional area continuously decreases from a maximum at their junction with lower end portions 19A which are downwardly inclined towards each other to provide an outlet to a minimum at their junction with upper end portions 19B which are inclined away from each other to provide a mouth or funnel to facilitate the introduction of heavy liquid into the chamber 12. That portion of the chamber 12 between a plane inclusive of the junctions of the outlet-forming portions 19A with the walls 19 and a plane inclusive of the junctions of the funnel forming portions 19B therewith are for the volume of heavy liquid to be used in forming the gradient. The chamber bottom 17 has a depending outlet 20 opening into the outlet defined by the portions 19A and located relatively near the front wall 18.

While the open upper end of the first chamber 11 provides ready access to the interior, the funnel established by the wall portion 19B of the chamber 12 make desirable some means to permit access to its interior. To that end, see FIGS. 2, 6, and 8, the side wall 19 proximate to the right hand end of the generator has a circular port hole 21 of substantial diameter closed by a plug 22 carrying an annular seal 23 and provided with a flange 24 dimensioned to be seated and held against the wall 19 spaced lugs 25. The plug flange 24 has notches 26, one for each lug 25 and spaced to enable the plug 22 to be inserted and then turned until the flange is secured by the lugs 25. A diametrically disposed rib 27 serves as a handle.

The base 10 is shown as having a platform 28 supported by two members 29 of U-shaped section extending substantially from end-to-end thereof, one member opening towards the front of the generator and the other opening in the opposite direction. The two members 29 are interconnected by spacers 30 and 31 extending lengthwise of the base between the side walls of the members 29 the upper side walls of which are secured against the undersurface of the platform 28 and the lower ones of which are provided with cushioned feet 29A.

The regulator 32, see FIGS. 3 and 4, includes a cylindrical base 32A and a cylindrical chamber 32B and at least the chamber 32B is shown of a transparent material. The base 32A has a shouldered upper end dimensioned to fit within the internally shouldered lower end of the chamber 32B and is provided with an annular seal 33. The base 32A fits within a hole 34 in the platform 32 so located that the base may be seated on the upper side wall of the front supporting member 29 and secured thereto by screw 35. The seat establishing portion of said upper side wall is provided with three holes 36.

The base 32A has three bores 37 of the same diameter extending upwardly through it and each is shown as having a counterbore in each end. A depending outlet 38 extending downwardly through a hole 36 is threaded in the lower counterbore of one bore 37. The inlets of the pressure regulator 32 are generally indicated at 39 and each includes a depending inlet member 39A identical to the outlet 38 and threaded in the appropriate one of the downwardly opening counterbores and extending through the appropriate hole 36 and tubular sections 39B of the same length, desirably of clear tubing, frictionally seated in the appropriate ones of the upwardly opening counterbores and extending close to the concave upper end of the chamber 32B with their upper ends in the same horizontal plane P, hereinafter referred to as the reference plane. The upper end of the chamber 32B is provided with a port 40 shown as closed by a cap 41 but which may have a syringe 42 connected thereto by a length of flexible tubing 43, see FIG. 7.

The base 13 of the chamber 11, see FIG. 5, is detachably bolted as at 43 to a plate 44 fixed on the upper end of a post 45 extending freely through a port 46 in the platform 28 and slidably guided for vertical movement in bores 30A and 31A in the spacers 30 and 31, respectively. The post 45 has a lengthwise channel 47 entered by a set screw 48 threaded through the rear supporting member 29 and the upper spacer 30 and operable to prevent rotation of the post 45 and also, when suitably tightened, to lock the post against vertical movement thus enabling the chamber 11 to be held in a selected vertical position. The outlet 16 of the chamber 11 and one of the inlets 39 of the pressure regulator 32 are interconnected by a length of flexible and desirably clear tubing 49. The tubing 49 extends freely through a port 50 in the upper side wall of the front supporting member 29 and is of sufficient length to permit the chamber 11 to be raised to the desired maximum extent.

The chamber 12, on the other hand, is anchored directly to the platform 28 with its base 17 bolted as at 51 to the platform between its supporting members 29. Its outlet 20 and the other inlet 39 of the pressure regulator 32 are interconnected by a conduit, desirably a length of flexible and desirably clear tubing 52 provided with an on-off valve 53 mounted on the outside of the front supporting member 29.

The outlet 38 of the pressure regulator 32 has a delivery conduit, generally indicated at 54 connected thereto, the conduit 54 including an on-off valve 55 and a mixer generally indicated at 56 in the order named and both mounted on the outside of the front supporting member 29. The mixer 56 is desirably but not necessarily of the motionless type with those made in accordance with U.S. Pat. No. 3,280,982 preferred.

At the outlet end of the delivery conduit 54 there is an adapter 57 for whatever conduit 58 is to be connected thereto for delivering the gradient to the receiver therefor. While such delivery may be made by gravity, the conduit 58 is shown as having a pump, generally indicated at 59, incorporated therein with the pump desirably but not necessarily of a peristaltic type. The conduit 58 is also shown as having an air vent 60 so that, in the event that the pump 59 is not shut down before the liquid in both chambers is spent, air will not be bubbled through the delivered gradient.

Before describing the operation of a gradient generator in accordance with the invention, it is important to note that the inlets 39 of the pressure regulator 32 open therein close to its closed upper end and in the horizontal reference plane P and that plane also includes the junctions of the walls 19 of the chamber 12 with their lower end portions 19A, the bottom of that portion of the heavy liquid chamber that contains the gradient forming volume.

In this connection, it may be assumed that a twelve liter gradient is wanted. The portion of the light liquid chamber 11 that is for the gradient forming volume, i.e., the portion below a plane inclusive of the junction of the side walls 15 with the upper end portions 15B, is then dimensioned to have a six liter capacity and desirably that portion of the chamber 11 above that plane has, by way of example only, a one liter capacity. In the case of the heavy liquid chamber 12, its capacity between planes inclusive of the junctions of its side walls with the outlet forming portions 19A and its funnel forming portions 19B is six liters and the capacity of the outlet portion of the chamber 12 is, by way of example only, one-half a liter.

Turning now to the usual mode of operating the generation of a gradient in accordance with the invention, the light liquid chamber 11 is raised relative to the heavy liquid chamber 12 by an amount equal to the ratio of the density of the heavy liquid to that of the light liquid the distance between the reference plane P and the junction of the side walls 15 with the funnel forming portions 15B being, say, 13.5 inches. This makes it possible for the flow to start from both chambers with reference to the maximum cross sectional area of the light liquid in the chamber 11 and the minimum cross sectional area of the heavy liquid in the chamber 12 and also achieves a pressure balance in the pressure regulator 25.

In operation, the valves 53 and 55 are closed and each chamber is filled with the appropriate liquid with the light liquid filling the chamber 11 in one mode of operation nearly to its brim and with the chamber 12 filled with the heavy liquid only to the junction between the side walls 19 and their funnel forming portions 19B. Since the light fluid chamber is open to and through the pressure rate regulator 32 and the valve 55 is closed, the light liquid enters the pressure regulator and compresses the air within it thus only partially filling the pressure regulator with the pressure therein equal to the density of the light fluid times its height relative to the reference plane P. As the inlets 39 open above the level of the liquid in the pressure regulator both chambers are effectively isolated from each other. When the valves 53 and 55 are open liquid starts to drain from the chamber 12 but does not flow into the pressure regulator until the product of its density and height with reference to the plane P balances the prevailing value in the light liquid chamber 11. When both values are the same, the two liquids mix in the pressure regulator.

With the delivery conduit 54 connected to whatever apparatus is going to use the generated gradient, the valves 53 and 55 opened, and the pump 59 turned on to permit flow from the pressure regulator 32, and through the mixer 56, liquids mix but with the flow initially a certain volume of the light liquid representing the excess volume with which the first chamber 11 is usually provided, and then a gradient since the liquids draining from the chambers 11 and 12 obey the hydrostatic relationship as previously explained.

It should be here noted that if delivery of the generated gradient is effected by gravity instead of by means of a pump, the same flow will follow but the pump 59 and air vent 60 would then be placed by a restrictor, a section of tubing, by way of example, having an inside diameter and length selected for the average viscosity and density of the gradient to be generated. By way of example and not of limitation, such a restrictor may be ¼ to 1 inch in length and having a one-sixteenth bore when the delivery conduit 54 has a bore of three-eighths of an inch to ensure a proper flow rate of about 500 ML/MN of the gradient is wanted.

The initial flow is from the chamber 11 because it is filled above the plane inclusive of the junction between its sides 15 and its upper end portion 15B. As flow will commence only when its fluid level is equal to or greater than its density times its height above the pressure reference plane P, the flow from both chambers can start together if both products are the same. Thus, with an excess of light liquid, a corresponding higher position of the upper level of the actual volume of the light liquid to be used in the generation of the gradient, or a corresponding lesser column of the heavy liquid, only light liquid will flow until its level drops to a point where the height times densities of the two liquids balance. At this point, both liquids will flow, maintaining a height relationship which is the inverse ratio of their densities with flow from the two chambers continuing with an increasing amount of the heavier liquid continuously mixing with a decreasing amount of the light liquid within the gradient forming portions of the two chambers until the light liquid is spent. It is obvious that the vertical position of the chamber 11 may be such that flow can start simultaneously from both chambers or that the generator may be operated with the flow initially from the second chamber 12.

The heavy liquid will, of course, continue to flow, unless stopped, with a preferred procedure being to continue the flow to provide a heavy liquid cushion under the delivered gradient. The delivery conduit 54 is then disconnected and the remaining heavy liquid recovered by discharging it into a suitable container. The amount of excess heavy liquid is at least the half liter in the outlet portion of the chamber 12 with the total amount determined by the initial offset of the light liquid chamber 11 relative to the plane P.

From the above, the importance of the pressure regulator 32 is apparent. One important function is that it establishes the pressure reference plane P. As the air in the regulator 32 becomes partially compressed, the liquids only partially fill it with two liquids mixing therein below the upper ends of the inlets 39, cross flow between the chambers 11 and 12 thus being positively prevented. As the two liquids combine within the regulator 32, the volumetric capacity of the regulator is as small as is consistent with the size of its inlet and outlet conduits.

Reference is now made to FIG. 9 wherein different concentration gradients are graphically illustrated. It will be noted that none is truly linear although so closely approaching that shape as to be acceptable as such. There are two reasons for this departure from a precisely linear shape of which one is that the liquids are typically of different viscosities but the error due to that factor is negligible for most purposes and can be minimized by reducing the flow rates or enhancing viscosity additives added to the light fluid.

The other reason is that the relationship of the volumes of the two liquids to be used in forming the gradient is such that their levels are not the same as the chambers drain with the consequence that when the first chamber has drained to its minimum cross sectional area, heavy liquid remains in the gradient forming portion of the second chamber. As a consequence, the density of the generated gradient increases at a uniformly faster rate than linear and terminates at a smaller volume than would be the case were it truly linear. This slightly concave departure from a linear gradient may be reduced by adjusting the levels in the chambers to minimize the effect of density differences.

Reference has been made to the fact that generators in accordance with the invention are capable of producing gradients of various shapes and volumes since the chambers are easily removed and replaced by chambers for other shapes and/or volumes.

In FIG. 8, there is shown an alternative to chamber replacement where a gradient of the same shape but of a smaller volume is wanted. In FIG. 8, the chamber 12 is shown as provided with an insert generally indicated at 61 fitted between its end walls 18.

The insert 61 has parallel first and second side walls 62 and 63, respectively, the side wall 62 seated against the side wall 19 of the chamber 12. The lower or bottom end 64 of the insert 61 seats against the proximate bottom portion 19A and the upper insert end wall 65 is dimensioned to engage the chamber side wall 19 at a selected height above the plane inclusive of the junctions of the walls 19 with their lower end portions 19B. The upper end wall 65 may be downwardly inclined for drainage purposes and its junction with the side wall 63 is notched as at 66 to effect communication between the upper end of the chamber 12 and the thus formed chamber portion that is for the smaller gradient forming volume of heavy liquid but is of the same shape as the original corresponding portion.

Because the chamber 12, in prqctice, has one side wall 19 provided with a porthole 21, normally sealed by the plug 22, as the only means permitting manual access to its interior, the insert 61 is shown as consisting of a series of identical sections 61A dimensioned for entry through the porthole 21 which is itself dimensioned to enable the sections to be introduced into the chamber 12 and the insert assembled in position from the inserts. Each section 61A has a beveled corner 66A at one end of the edge defined by the junction of the walls 65A and 63A, the corner 66A establishing the notch 66 when the insert 61 is assembled in the chamber 12.

It will be appreciated from FIG. 1 that no change is necessary in the case of the chamber 11 as the desired shape is assured with whatever smaller volume of light liquid is used therein.

Figure 10:
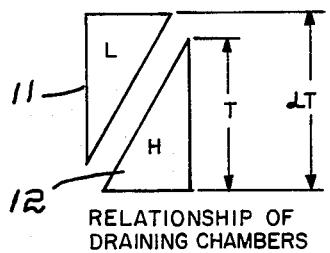
FIG. 10 is a schematic view for use with the expression by which a gradient slope may be calculated.

The shape of the gradient may be calculated from the following expression which describes the flow phenomena from the light and heavy chambers. See FIG. 10.

$$V = \frac{1}{2}\left[1 + 2\epsilon - \epsilon^2 + 2(\epsilon - \frac{1}{\beta} - 1)\gamma + (\frac{1}{\beta^2} - 1)\gamma^2\right]$$

-continued
$$C = \frac{\beta - \gamma}{\beta(\gamma - \epsilon + 2) - \gamma}$$

Where:
 $V$ = Volume fraction (instantaneous)
 $\epsilon$ = Offset of light fluid chamber above the reference plane $\div$ T
 $\beta$ = Heavy fluid density $\div$ light fluid density
 $\alpha$ = Height of light fluid $\div$ T
 $c$ = Concentration, % heavy fluid (instantaneous)
 $T$ = the height of the chambers

I claim:

1. A hydrostatic liquid concentration gradient generator including first and second chambers open at their upper ends, the first for a first liquid and the second for a second liquid, said chambers including portions of the same volumetric capacity and of a cross section that decreases vertically in area in the same manner from a maximum at one end to a minimum at the other with the smallest cross sectional area of the first chamber portion and the largest cross sectional area of the second chamber portion the bottoms thereof, and a pressure regulator including an outlet and inlets, one inlet for each chamber and placed in communication with the bottom thereof and both inlets opening in the pressure regulator above the outlet thereof independently of each other and at the same level to establish a pressure reference plane, the inlet in communication with the second chamber and the outlet each including an on-off valve, and the second chamber positioned with the maximum cross sectional area of its tapering portion in said pressure reference plane.

2. The hydrostatic liquid concentration gradient generator of claim 1 in which the inlets and the outlet of the pressure regulator are of the same diameter and the cross sectional area and height of the pressure regulator are such that with the outlet valve closed, the liquid volume flowing into the regulator creates a flow-blocking pressure and the volume to the liquids mixing therein when the valves are open is insufficient to result in any material departure from the constancy in the rate of concentration change that is necessary for a generated gradient.

3. The hydrostatic gradient generator of claim 1 and supporting means to which the first chamber is attached and which is vertically adjustable to offset the first chamber relative to the second chamber and said reference plane.

4. The hydrostatic gradient generator of claim 1 in which the first chamber includes an upper portion dimensioned to enable the first chamber to contain more first liquid than is required for the production of the gradient.

5. The hydrostatic gradient generator of claim 1 in which the second chamber includes a lower portion dimensioned to enable the second chamber to contain more heavy liquid than is required for the production of the gradient.

6. The hydrostatic gradient generator of claim 1 in which at least one of said chambers includes a base, front and rear end walls, and a pair of side walls, both of said side walls inclined inwardly in the same manner towards each other to provide said chamber portion, and said base including an outlet to which the appropriate one of the pressure regulator inlets is connected.

7. The hydrostatic gradient generator of claim 6 in which the chamber is the first chamber and said side walls include upper and lower end portions, said lower end portions defining a narrow outlet channel into which said outlet opens, and said upper end portions vertical and defining with the upper end portions of the end walls an upper chamber portion enabling the first chamber to have a light liquid capacity in excess of that to be used in forming the gradient.

8. The hydrostatic gradient generator of claim 6 in which the chamber is the second chamber and said side walls include upper and lower end portions, said lower end portions downwardly inclined towards each other and towards said outlet and defining with said end walls a lower chamber portion for a predetermined volume of heavy liquid in excess of that to be used in forming the gradient, and the upper end portions are inclined upwardly and away from each other to provide a funnel entrance.

9. The hydrostatic gradient generator of claim 8 in which one of said walls has a porthole, a plug sealing said porthole, and said plug and said one wall includes means releasably engaged to hold said plug in said porthole.

10. The hydrostatic gradient generator of claim 8 and an insert for said second chamber extending from one end wall to the other, said insert having parallel side walls of which one is seated against one chamber side wall, a lower end seated on the proximate lower end portion of the chamber and an upper end in contact with the other chamber side wall a predetermined distance above a plane inclusive of the junction of the chamber side walls and the lower portions thereof and the second chamber includes means permitting introduction of the circuit into or its removal from the chamber.

11. The hydrostatic gradient generator of claim 10 in which the access means is a porthole in one chamber side wall and includes a removable plug, and the insert consists of a series of identical sections, each dimensioned to be placed in position in the chamber through the porthole.

12. The hydrostatic gradient generator of claim 1 and a base to which the chambers are detachably attached, and said pressure regulator is attached to said base between said chambers.

13. The hydrostatic gradient generator of claim 12 in which the base includes a plate provided with a depending post, means connecting said post to said base for vertical movement relative thereto, and means to lock said post in any selected vertical position, said first chambr detachably attached to said plate.

14. The hydrostatic gradient generator of claim 13 in which the base includes a platform and a pair of transversely spaced supporting members extending lengthwise thereof, spacing means below said platform and interconnecting said supporting members, a plate including a post, said post extending vertically through said platform and supported by said spacing means to slide vertically relative thereto, and means operable to lock said post to one of said spacing means, said first chamber attached to said plate.

15. The hydrostatic gradient generator of claim 1 and an elongated base that is substantially I-shaped in cross section, each chamber is mounted on said base adjacent an end thereof, said pressure regulator is mounted on said base centrally thereof and on one side of the central part of the base, its inlets connect to the chamber outlets through said base on the same side thereof and a delivery conduit connected to the outlet of the pressure regulator and connected to the base on the same side thereof.

* * * * *